United States Patent [19]
Egee et al.

[11] Patent Number: 4,875,175
[45] Date of Patent: Oct. 17, 1989

[54] METHOD AND DEVICE FOR ANALYZING AND MEASURING PHYSICAL PARAMETERS OF A LAYERED MATERIAL BY THERMAL RADIOMETRY

[75] Inventors: Michel Egee; Robert Dartois, both of Reims; Jean Marx, Cormontreuil; Etienne Merienne, Reims; Marcel Regalia, Reims; Philippe Poplimont, Reims; Etienne Van Schel, Reims, all of France

[73] Assignee: Universite de Reims Champagne-Ardenne, Reims, France

[21] Appl. No.: 11,497

[22] Filed: Feb. 5, 1987

[30] Foreign Application Priority Data

Feb. 6, 1986 [FR] France .................. 86 01613

[51] Int. Cl.$^4$ .................. G01N 21/41; G06F 15/20
[52] U.S. Cl. .................. 364/551.01; 364/557; 364/563; 73/601; 378/89
[58] Field of Search .............. 364/498, 551, 557, 563, 364/525, 524, 551.01; 374/5, 7, 17, 55, 57, 117, 121, 124, 127, 129, 130; 356/432, 435, 445–446, 237; 250/338, 341, 266; 73/601, 603, 606, 643, 657; 378/89

[56] References Cited

U.S. PATENT DOCUMENTS

| | | | |
|---|---|---|---|
| 4,453,225 | 6/1984 | Ford | 364/551 |
| 4,594,511 | 6/1986 | Cooper et al. | 250/341 |
| 4,632,561 | 12/1986 | Rosencwaig et al. | 374/5 |
| 4,679,946 | 7/1987 | Rosencwaig et al. | 374/5 |

FOREIGN PATENT DOCUMENTS 8303303 9/1983 Finland .
0124224 11/1984 France .

OTHER PUBLICATIONS

G. Busse, "Optoacoustic Phase Angle Measurement for Probing a Metal", Nov. 15, 1979, pp. 759–760.
G. Busse, "Thermal Wave Remote and Nondestructive Inspection of Polymers", Applied Physics Letters, Aug. 15, 1983, pp. 355–357.
Aithal et al, "Photoacoustic Characterization of Subsurface Defects in Plasma-Sprayed Coatings", Thin Solids Films, Sep. 1984, pp. 153–158.
Lopatkin et al, "Laser Modulation Photothermal Radiometer—a New Method for Measuring Weak Absorption in Bulk Materials and Coatings", Feb. 1985.

Primary Examiner—Parshotam S. Lall
Assistant Examiner—Ellis B. Ramirez
Attorney, Agent, or Firm—Blakely, Sokoloff, Taylor & Zafman

[57] ABSTRACT

A method and a device are used to analyze and measure by means of radiometry physical parameters of a layered material. These parameters include the absorptivity B, the diffusivity A of the surface layer and the thermal resistance R of the interface between the two layers. A sample of the material is excited by means of a flux of thermal energy amplitude modulated at a high frequency and a low frequency. The parameters are computed from the measured phase shift and amplitude of the resulting thermal signal. The method and the device are applicable to non-destructive testing of industrial products.

22 Claims, 6 Drawing Sheets

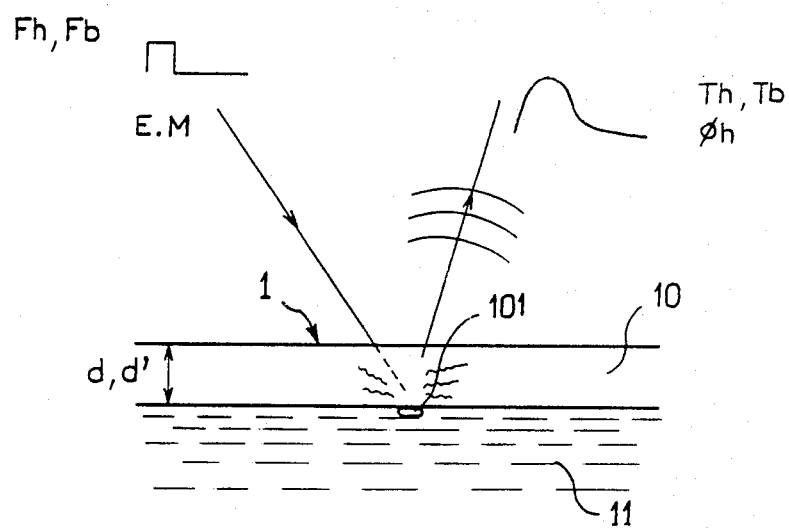
FIG_1
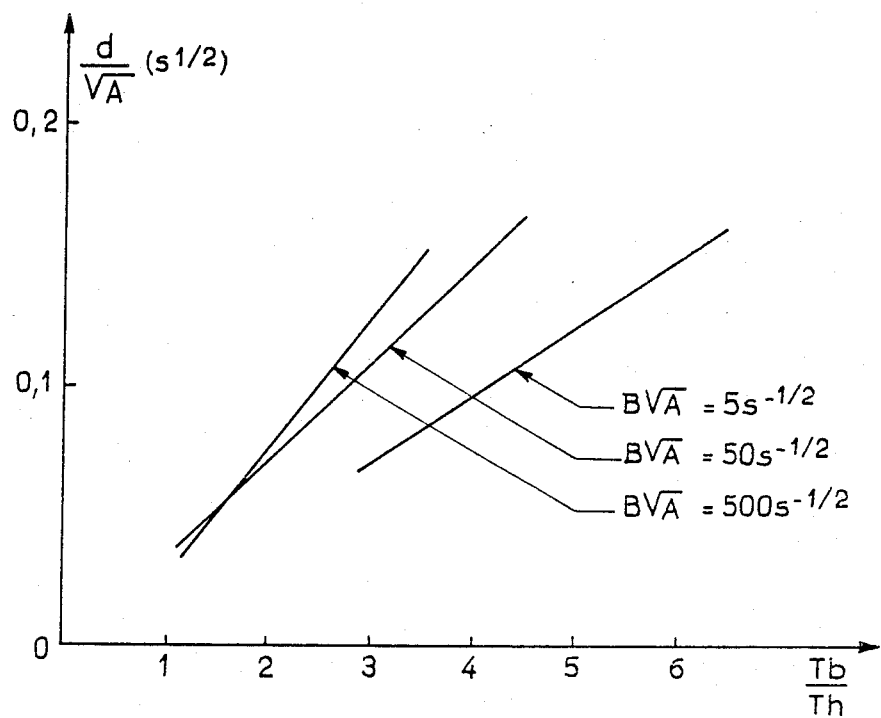
FIG_2

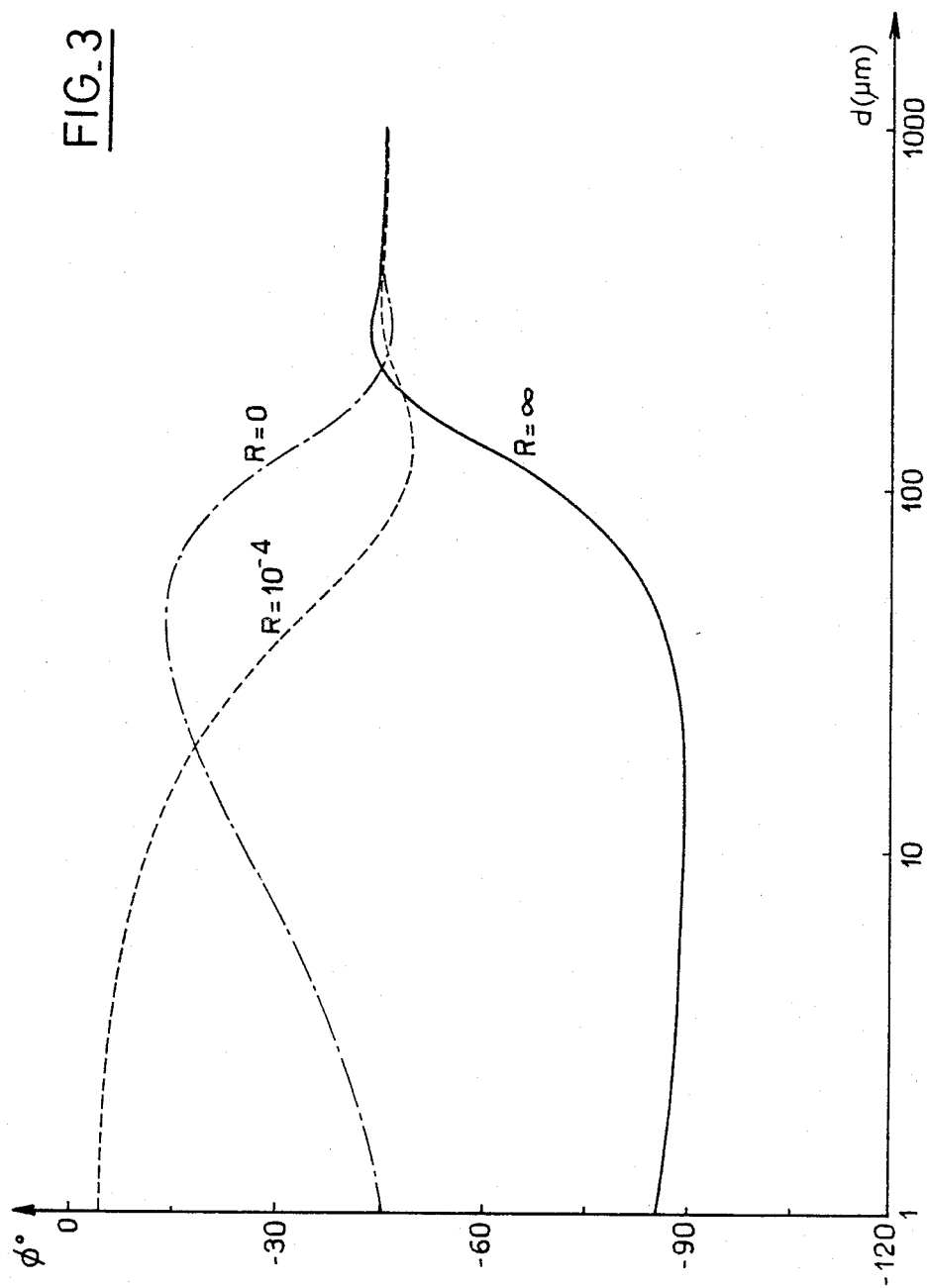

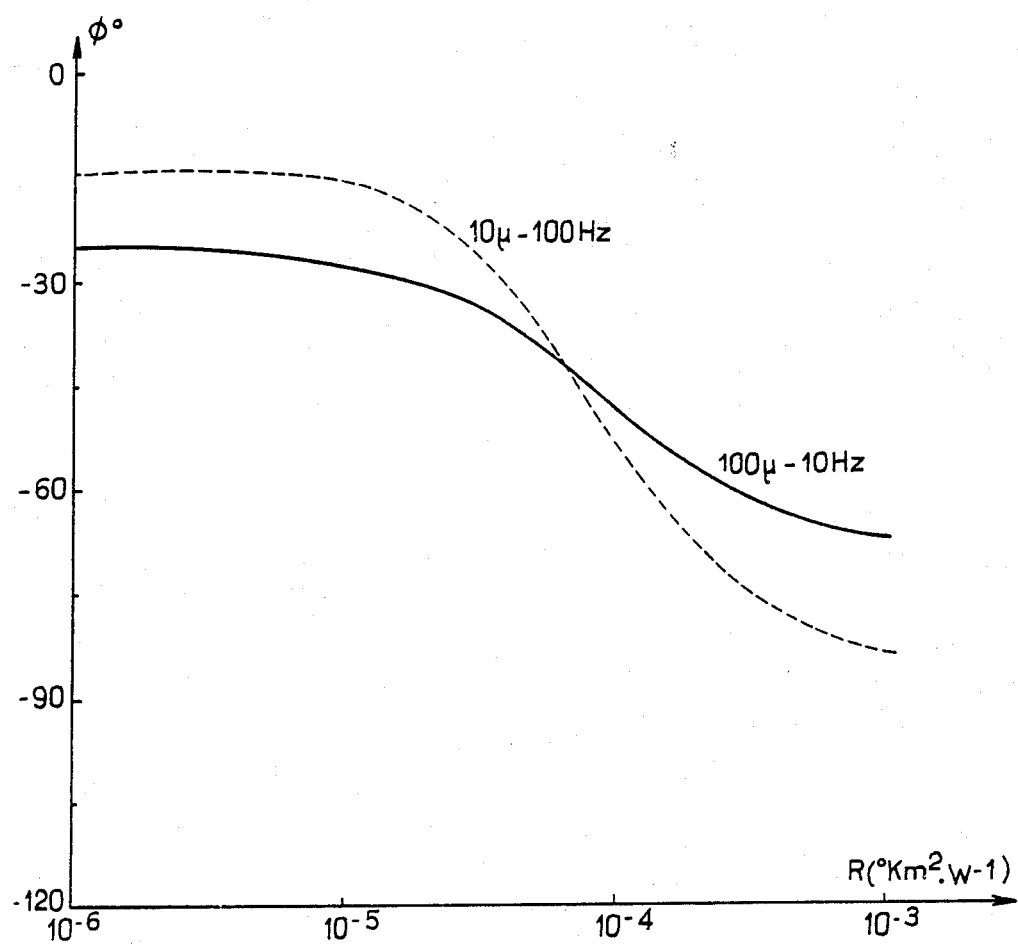
FIG_4a

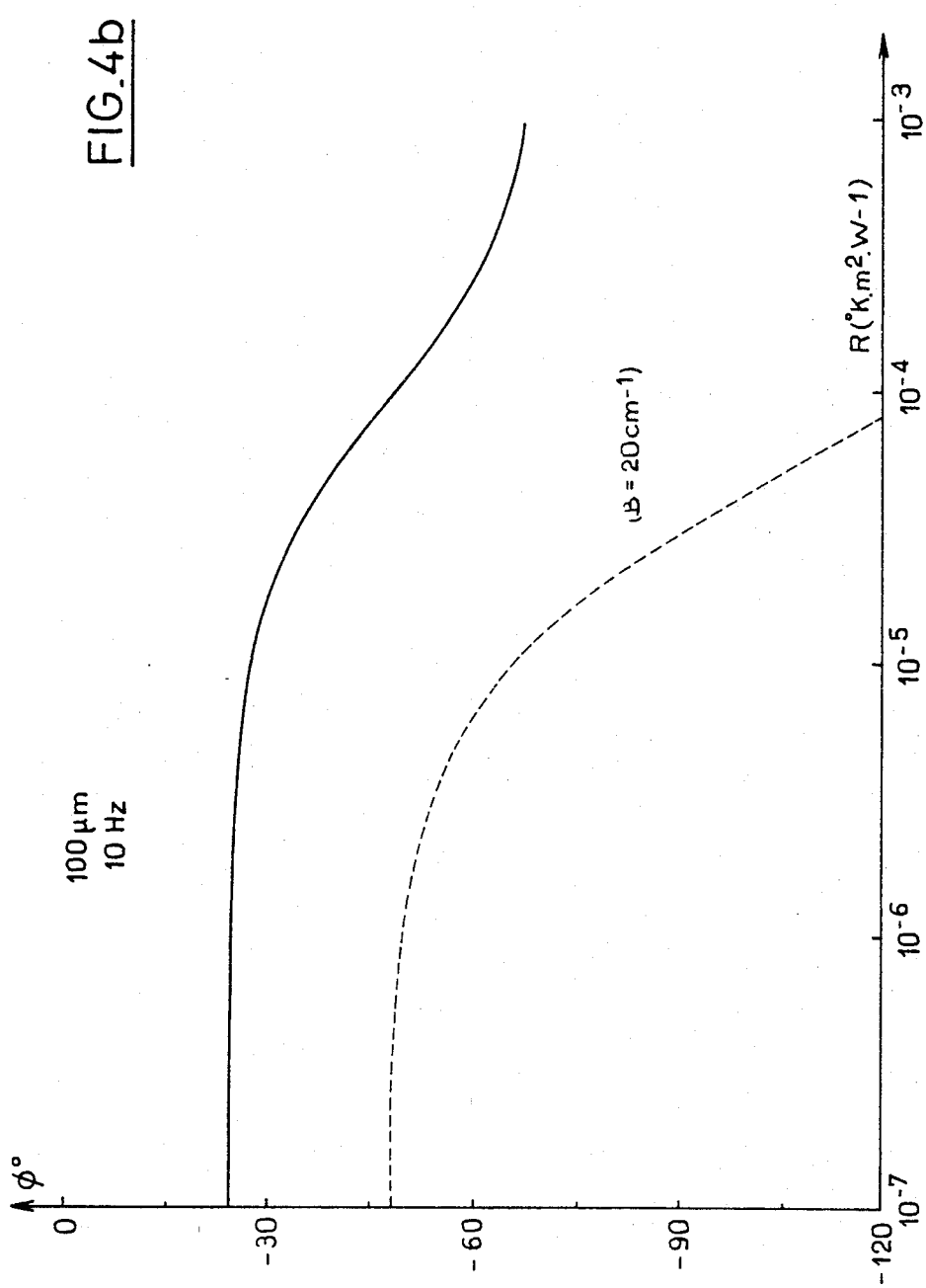

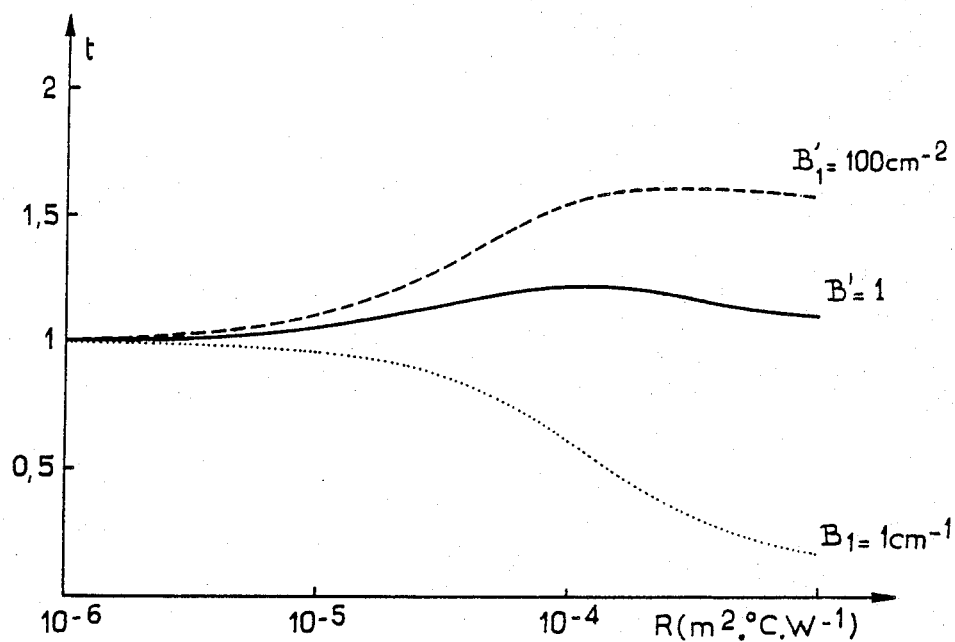
FIG_5a
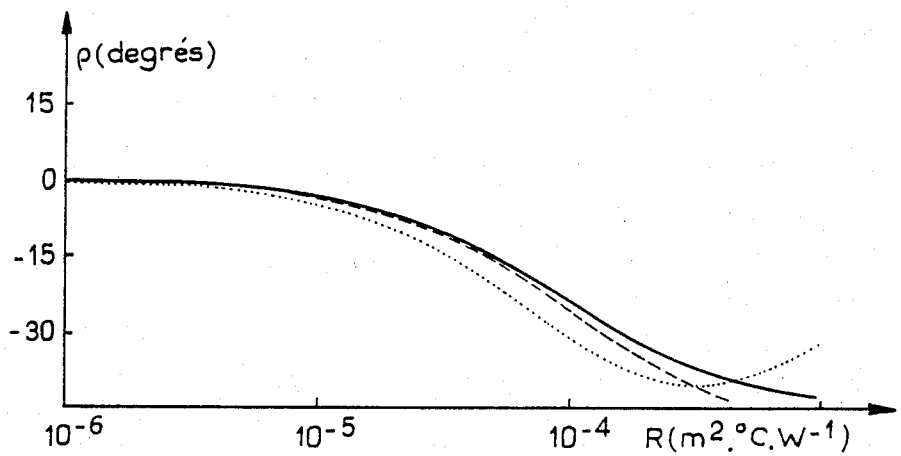
FIG_5b

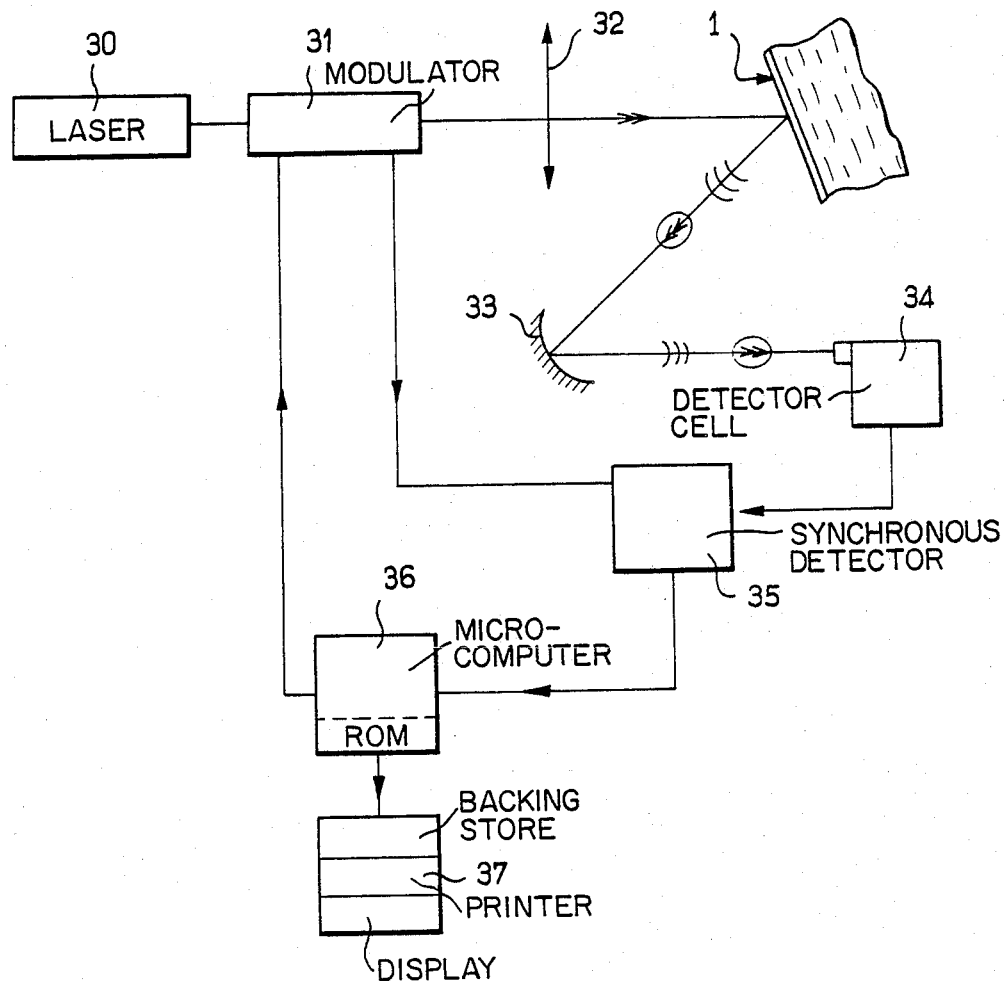
FIG_6

METHOD AND DEVICE FOR ANALYZING AND MEASURING PHYSICAL PARAMETERS OF A LAYERED MATERIAL BY THERMAL RADIOMETRY

BACKGROUND OF THE INVENTION

1. Field of the Invention

The present invention relates to a method and a device for analyzing and measuring physical parameters of a layered material by thermal radiometry.

2. Description of the prior art

The technique of analyzing materials of this type by thermal radiometry, especially photo-thermal radiometry, has been the subject of recent work directed towards measuring the thickness of a coating layer.

For a detailed and recent bibliography of publications relating to this work reference may be had to "3" topical meeting on photoacoustic and photothermal spectroscopy—Paris 5-8 April 1983. Journal de Physique, Supplement to facsicle 10, C6, 1983.

The principle of this method is to observe variations in the thermal radiation emitted by the surface of a sample illuminated by a light source amplitude modulated according to a periodic law. The radiation absorbed periodically the sample is converted by it into heat and produces thermal radiation.

This principle is applied to measuring the thickness of opaque thin films, as described in particular in European patent application EP-A-0 124 224 published Nov. 7, 1984.

According to the technique described in this patent application, two laser beams, an excitation beam and an analysis beam, are focussed on the same analysis point of the sample. The excitation beam is modulated at a very high frequency, 10,000 Hz, and the analysis beam serves to detect the thermal radiation generated as a result of excitation of the sample.

Although this method can prove satisfactory in the application envisaged, it uses a complex device because of the necessity for two laser beams and the need to focus these on the analysis point.

Also, being limited to excitation by means of coherent electromagnetic radiation, it makes no provision for widespread application in an industrial environment and in the broadest possible range of situations, because of the necessarily limited number of emission wavelengths of the excitation laser that can be used and the resulting limitations on the emission band spectrum.

An object of the present invention is to alleviate the aforementioned disadvantages by employing a method and a device for analyzing and measuring parameters of a layered material by radiometry in which the analysis laser beam is dispensed with.

Another object of the present invention is the implementation of a method and a device for analyzing and measuring parameters of a layered material in which the sample to be analyzed is excited by any appropriate means given the nature of the sample to be analyzed.

Another object of the present invention is the implementaton of a method and a device for analyzing and measuring parameters other than the thickness of the coating layer of a layered material, such as absorptivity, diffusivity and the thermal resistance of the interface beween the layers.

SUMMARY OF THE INVENTION

In one aspect, the present invention consists in a method of analyzing and measuring by thermal radiometry physical parameters of a layered material comprising a base layer and a surface layer, wherein to determine said parameters such as the absorpivity B and diffusivity A of said surface layer and the thermal resistance R of the interface between said two layers of a sample relative to a reference sample having a surface layer of known thickness d' the method consists in:

(a) exciting the surface layer side of said reference sample by means of a flux of thermal energy amplitude modulated according to a period law at a high frequency Fh very much greater than a value for which the thermal diffusion length l' of said surface layer is small relative to the thickness d' of said surface layer.

(b) detecting the thermal signal generated by said reference sample as a result of absorption and measuring the amplitude Th and phase shift $\phi h$ of said thermal signal relative to the amplitude modulation excitation signal;

(c) exciting the surface layer side of said reference sample by means of a flux of thermal energy amplitude modulated according to a period law at a low frequency Fb such that said thermal diffusion length l' of said surface layer is approximately equal to its thickness;

(d) detecting the thermal signal generated by said reference sample in response to said excitation and measuring the amplitude Tb of said thermal signal, and (e) determining the parameter A from the ratio of the amplitudes of said thermal signal at said low and said high frequencies, Tb/Th, and from the equation:

$$B\sqrt{A} = \frac{\tan\left(\phi + \frac{\pi}{2}\right)}{1 - \tan\left(\phi + \frac{\pi}{2}\right)} \sqrt{4\pi Fh}$$

by interpolation using an array of values $d/\sqrt{A}$, Tb/Th, $B\sqrt{A}$ (FIG. 2) and then determining the parameter B.

In another aspect the present invention consists in a device for implementing a method of analyzing and measuring by thermal radiometry physical parameters of a layered material comprising a base layer and a surface layer as defined in the preceding paragraph, comprising:

(a) means for exciting the surface layer side of a sample of the material by means of a flux of thermal energy amplitude modulated according to a periodic law at least at a high frequency Fh and a low frequency Fb, said high frequency Fh being very much higher than a frequency for which the thermal diffusion length of said surface layer is small relative to the thickness of said surface layer and said low frequency Fb being such that the thermal diffusion length of said surface layer is approximately equal to its thickness;

(b) means for detecting the thermal signal generated by said sample and means for measuring the amplitude Th, Tb and the phase shifts $\phi h$, $\phi b$ of said thermal signal relative to the amplitude modulation excitation signal;

(c) means for storing said signals and computing:

the diffusivity A of said surface layer from the ratio of the amplitudes of said thermal signal at said low and said high frequencies, Tb/Th, and the equation:

$$B\sqrt{A} = \frac{\tan\left(\phi + \frac{\pi}{2}\right)}{1 - \tan\left(\phi + \frac{\pi}{2}\right)} \sqrt{4\pi Fh}$$

by interpolation from an array of values $d/\sqrt{A}$, Tb/Th, $B\sqrt{A}$, and then computing the absorptivity parameter B;

the thickness d of said surface layer from said array of values $\phi$, R and d, where $\phi$ represents the measured phase shift, or from said array of values $d/\sqrt{A}$, Tb/Th, $B\sqrt{A}$;

the absorptivity B of said surface layer from the equation:

$$B = \frac{\tan\left(\phi + \frac{\pi}{2}\right)}{1 - \tan\left(\phi + \frac{\pi}{2}\right)} \sqrt{\frac{4\pi Fh}{A}}$$

the diffusivity A of said surface layer from the equation:

$$A = \frac{1}{B^2} \left(\frac{\tan\left(\phi + \frac{\pi}{2}\right)}{1 - \tan\left(\phi + \frac{\pi}{2}\right)}\right)^2 \cdot 4\pi Fh$$

the thermal resistance R of the interface between said two layers from said array of values $\phi$ and R.

Storage means for the aforementioned signals and computing means serve to compute the diffusivity A and the absorptivity B of the surface layer, its thickness d and the thermal resistance R of the interface between the two layers.

The method and the device of the invention find applications in non-destructive and contact-less testing of layered materials in the most diverse sectors of industry, including mineral, organic and metal coatings composite film materials, semiconductors and all types of opaque semi-transparent materials. Further, subject to minimal adaptation, the method and the device of the invention may with advantage be used in hematology and in bio-engineering to determine corresponding parameters of solids, semi-solids, liquids, powders, gels, living tissues and physiological liquids.

The invention will be better understood from the following description given with reference to the appended drawings.

BRIEF DESCRIPTION OF THE DRAWINGS

FIG. 1 is a schematic diagram showing the method of the invention.

FIG. 2 shows an array of values for theoretical parameters such as the thickness d, the absorptivity B, the diffusivity A and the amplitudes of the thermal radiation emitted by the material following excitation.

FIG. 3 shows an array of theoretical values for the phase shift $\phi$, the thickness d of the surface layer of the material and the thermal resistance R of the interface between the two layers of the material.

FIGS. 4a and 4b show an array of theoretical values for the phase shift $\phi$ between the thermal radiation emitted by the sample and the excitation signal, the thermal resistance R of the interface between the two layers respectively for specific values of the thickness d of the surface layer of the material for specific values of the modulation frequency and for different kinds of surface layer, when an opaque or semi-transparent material constitutes the surface layer or, when the material constituting the surface layer is the same for a given sample, for different values of the wavelength of the electromagnetic radiation corresponding to opacity and semi-transparency of the material constituting the surface layer when the material is excited by means of electromagnetic radiation.

FIGS. 5a and 5b respectively show an array of theoretical values of the absorptivity of the material constituting the surface layer, the thermal resistance of the interface between the two layers, the ratio of the amplitudes of the thermal radiation emitted by the material following excitation and the phase shift between the aforementioned thermal radiation and the excitation signal.

FIG. 6 is a block diagram of a device for implementing the method in accordance with the invention.

DESCRIPTION

The method in accordance with the invention of analyzing and measuring physical parameters of a layered material will first be described with reference to FIG. 1.

In this figure the material 1 is shown as consisting of a base layer 11 and a surface layer 10. This type of material is routinely used in most sectors of industry where a coating is applied by enamelling, hot spraying or any other conventional technique onto a substrate. The expression "layered material comprising a base layer and a surface layer" is intended to mean any industrial material or physiological product in which a base area and a surface area are separated by an intermediate area in which there is a gradient of the concentration of the constituent components of the base and surface areas.

The purpose of the method in accordance with the invention is to determine physical parameters of the material and in particular of its surface layer, parameters such as the absorptivity B, the diffusivity A of the surface layer and the thermal resistance R of the interface between the two consituent layers 10 and 11 of the material. The aforementioned parameters, in particular the absorptivity B and the diffusivity A of the surface layer, are relevant to the absorptivity and the diffusivity of the surface layer subjected to the excitation flux of thermal energy.

The method of the invention consists in using a flux of thermal energy amplitude modulated according to a period law to excite a reference sample comprising a surface layer of known thickness d', at an amplitude modulation frequency Fh, referred to as the high frequency, which is very much higher than a value for which the thermal diffusion length $l'$ of the surface layer is small relative to its thickness $d'$.

The thermal signal generated by the sample 1 as a result of absorption is detected and the ampltude Th and the phase shift $\phi h$ of the thermal signal relative to the amplitude modulation excitation signal are then measured. It should be noted that in this description non-indexed variables and parameters correspond to the theoretical values calculated from arrays of values obtained from a mathematical model whereas the same parameters and variable when indexed correspond to measured values.

The sample 1 is also excited on the surface layer side by maens of a flux of thermal energy amplitude modulated according to a period law at an amplitude modulation frequency Fb, referred to as the low frequency, such that the thermal diffusion length $l'$ of the surface layer is approximately equal to its thickness $d'$. The modulation frequencies are also denoted Fh, Fb in FIG. 1. The thermal signal generated by the sample subjected to this excitation is detected and the amplitude Tb of this signal at the modulation frequency in question is then measured. The diffusivity parameter A relative to the surface layer can then be determined from the ratio of the amplitudes of the thermal signal, or thermal radiation, at the low and high frequencies, Tb/Th, and the equation:

$$B\sqrt{A} = \frac{\tan\left(\phi + \frac{\pi}{2}\right)}{1 - \tan\left(\phi + \frac{\pi}{2}\right)} \sqrt{4\pi Fh}$$

by interpolation from an array such as shown in FIG. 2 or an array of value $d/\sqrt{A}$, Tb/Th, $B\sqrt{A}$. The parameter B relating the absorptivity of the surface layer 10 may then be determined in an analogous way.

Note that the parameters $d/\sqrt{A}$ and $B\sqrt{A}$ are respectively homogeneous to a time to the power $\frac{1}{2}$ and $-\frac{1}{2}$.

The modulation frequencies Fh and Fb for a material of a given kind, in particular a given kind of surface layer, may advantageously be chosen knowing the order of magnitude of the diffusivity A which is approximately $10^{-4}$ to $10^{-5}$ for metals and $10^{-6}$ to $10^{-7}$ for dielectric materials. For a given known thickness $d'$ of the surface layer of the reference sample it is possible to deduce a working high frequency Fh substantially equal to $$Fh = \frac{10 \cdot A}{\pi \cdot d'^2}.$$

The low modulation frequency Fb may then be chosen with a value such that the diffusion length $l'$ is of the same order of magnitude as the thickness $d'$, that is to say $$Fb \simeq \frac{A}{\pi \cdot d'^2}.$$

To give a non-limiting example, the high and low modulation frequencies Fh, Fb may be chosen, depending on the application in question, in a range of frequencies between 10 Hz and 300 Hz. The modulation frequency values having been chosen for a given type of material and for a given reference sample, the implementation of the method as previously defined on the reference sample makes it possible to determine with a high degree of accuracy the values of the diffusivity A and absorptivity B parameters of the corresponding surface layer.

When the method of the invention is implemented the parameter $d/\sqrt{A}$ is computed on the assumption that the order of magnitude of the diffusivity of the material constituting the surface layer is known, this parameter having a second order influence in this computation. Note also that using only the ratio of the thermal signal amplitudes at the high and low frequencies eliminates the need to know a number of parameters independent of the modulation frequency, such as the monochromatic reflectivity of the surface layer/air interface, the infra red emissivity of the surface layer, the level of the illumination on the sample when the excitation thermal flux is obtained by means of electromagnetic radiation, and the gain factor of the detection system.

The method of the invention may also be used to analyze and measure a physical parameter of the surface layer of the material such as the thickness d of any sample of the material, the corresponding absorptivity B and diffusivity A parameters having been determined using the method of the invention as described previously. In this case, the thermal resistance R should preferably be assumed to be negligible, or of low value, that is to say: the method of the present invention may advantageously be applied to layered materials in which there are very few inclusions, foreign bodies or detachments at the interface between the two layers.

According to the method of the invention, the diffusivity A and absorptivity B parameters being known or determined as previously, any sample of the material for which the thickness d of the surface is to be determined is subjected to stages analogous to the stages as previously described relative to the reference sample. The thickness d of the surface layer of the sample of material can then be determined from the array of values for $d/\sqrt{A}$, Tb/Th, $B\sqrt{A}$ shown in FIG. 2.

In an alternative embodiment of the method as previously described, the sample of material is subjected to a stage analogous to that to which the reference sample was subjected to determine the thermal signal generated in response to excitation of the sample at the low modulation frequency Fb and the method further consists in measuring the phase shift $\phi b$ of the thermal signal relative to the amplitude modulation excitation signal of frequency Fb. As already mentioned, of course, $\phi b$ represents the measured phase shift of the thermal signal relative to the amplitude modulation excitation signal.

The thickness d of the surface layer 10 of the sample of the material can then advantageously be determined from the array of values $\phi$, R, d as shown in FIG. 3 where $\phi$ represents the theoretical value of the phase shift.

An advantageous embodiment of the method in accordance with the invention will now be described in the case, for example, of an application for monitoring the treatment of the surface layer, this treatment affecting the actual value of the absorptivity parameter B, for example, industrial treatments of this type possibly consisting in treatments to anneal the material, or aging treatments to enable the surface layer to be analyzed at a later stage by means of spectral reflectivity techniques.

In the method now to be described it is assumed that the diffusivity parameter A of the surface layer is known or has been determined in the way previously described; the parameters comprising the thermal resistance R of the interface between the two layers and the thickness d of the surface layer can take any values, provided that the thickness is greater than the diffusion length l of the same surface layer. In this embodiment of the method in accordance with the invention, a sample of the material is subjected on the surface layer side to excitation by means of a flux of thermal energy amplitude modulated according to a periodic law at a frequency substantially equal to the frequency Fh. The thermal signal generated as a result of absorption by the surface layer of the material is detected and the phase shift $\phi h$ of the thermal signal relative to the amplitude modulation excitation signal is measured.

The absorptivity B of the surface layer may then advantageously be determined from the equation:

$$B = \frac{\tan\left(\phi + \frac{\pi}{2}\right)}{1 - \tan\left(\phi + \frac{\pi}{2}\right)} \sqrt{\frac{4\pi Fh}{A}}$$

This equation may be written in a simpler form:

$$B\sqrt{A} = \frac{-\sqrt{4\pi Fh}}{1 + tg\phi}$$

This alternative embodiment of the method in accordance with the invention may of course be employed in an analogous manner to determine the diffusivity parameter A of the surface layer of a sample of a material when the absorptivity B of the latter has been determined from a reference sample, as previously described, for example. To this end the sample of the material is also subjected on the surface layer side to excitation by means of a flux of thermal energy amplitude modulated by a frequency substantially equal to the frequency Fh. The thermal signal generated as a result of absorption by the material is detected and the phase shift $\phi h$ of this thermal signal relative to the amplitude modulation excitation signal is measured. The diffusivity A of the surface layer may then be determined from the equation:

$$A = \frac{1}{B^2} \left( \frac{\tan\left(\phi + \frac{\pi}{2}\right)}{1 - \tan\left(\phi + \frac{\pi}{2}\right)} \right)^2 \cdot 4\pi Fh$$

This equation can also be derived from the previous simplified equation.

An advantageous embodiment of the method in accordance with the invention will now be described in the case where the thermal resistance R of the interface between the two layers is to be determined.

In this embodiment of the method it is assumed that the parameters of the material such as the thickness d, the diffusivity A and the absorptivity B are known or have been determined using one of the embodiments of the method as previously described.

Using the method of the invention, the material or a sample of the material is subjected on the surface layer 10 side to excitation by means of a flux of thermal energy amplitude modulated according to a periodic law at a frequency substantially equal to the low frequency Fb. The thermal signal generated as a result of absorption by the material is detected and the phase shift $\phi b$ of the thermal signal relative to the amplitude modulation excitation signal is then measured. The thermal resistance R of the interface between the two layers can then be determined from an array of values $\phi$, R such as shown in FIGS. 4a and 4b.

It will be seen that in these figures the parameters concern the phase shift $\phi$ expressed in degrees, the thermal resistance R expressed in °K.m²/W, for different values of the excitation signal modulation frequency parameter and the corresponding thickness of the surface layer expressed in µm in the case of FIG. 4a, the parameters in question concerning the phase shift $\phi$ expressed in degrees, the thermal resistance R expressed in the same units as FIG. 4a and various values of teh absorptivity parameter B related to the quality of opacity or semi-transparency of the surface layer.

In accordance with the invention, the stages during which the reference sample or the sample of the material is excited by means of a flux of thermal energy that is amplitude modulated may be simultaneous or successive. In the latter case the stages may be applied in a predetermined sequence, that is to say excitation at the low modulation frequency and then the high frequency (Fg, Fh) or excitation at the high modulation frequency and then the low frequency (Fh, Fb).

According to one characteristic of the method in accordance with the invention, the excitation flux of thermal energy may be generated by means of a modulated flow of heat-exchange fluid, for example, or by Joule effect heating when the surface layer is an electrical conductor. This latter embodiment of the method in accordance with the invention is advantageous in the specific case of testing crimping of metal or similar objects.

According to an advantageous variant of the aforementioned characteristics, the excitation flux of thermal energy may be obtained by means of electromagnetic radiation that the surface layer can absorb to a greater or lesser degree. The term electromagnetic radiation is to be understood as advantageously but not exclusively denoting coherent or non-coherent radiation at wavelengths in the visible spectrum.

Where electromagnetic radiation is used, the wavelength of the radiation is preferably but no necessarily chosen to correspond to the semi-transparency band of the surface layer. This can enable better photo-thermal transfer between the incident radiation and the surface layer and, as a consequence of this, increased sensitivity for contact resistance measurements, actually measurements of the thermal resistance, as can be seen from FIGS. 5a and 5b in particular. These figures provide a comparison, for the same enamel surface layer on a sheet metal base layer, of the difference between the trend for the ratio of the amplitudes measured at the high and low frequencies and of the phase shift $\phi$ relative to the amplitude modulation excitation signal, according to whether the excitation electromagnetic radiation is chosen to have a wavelength corresponding to opacity or to semi-transparency of the surface layer. The sensitivity for measuring low contact resistance may be significantly improved. Also, this choice makes it possible to improve the sensitivity of thickness measurements.

In the case of measuring the diffusivity parameter A, it would, however, be advantageous to choose electromagnetic radiation having a wavelength corresponding to a high degree of opacity of the surface layer in order to improve the measurement sensitivity.

To implement the method of the invention as previously described it is, of course, advantageous to carry out a stage calibration phase consisting in subjecting a calibrated sample to the excitation flux of thermal energy; this can be any sample given a known phase shift, such as a thermally thick sample absorbing only at the surface, producing a specific phase shift of substantially 45° between the thermal signal generated as a result of absorption by the material of the calibrated sample and the amplitude modulation excitation signal.

To this end it is advantageous to use either a thick slab of glass blackened with lamp black or a block of metal, such as lead, for example, guaranteeing in both cases surface absorption and internal thermal transfers by conduction only. The aforementioned calibrated sample has to be sufficiently thick for its thermal diffusion length to remain less than its thickness at the low modulation frequencies employed.

An advantageous embodiment of the device in accordance with the invention will now be described with reference to FIG. 6.

In this figure, the device for implementing the method advantageously comprises means 30, 31 for exciting the surface layer side of a sample 1 of material by means of a flux of thermal energy amplitude modulated according to a period low at least at a first modulation frequency Fh, or high frequency, and a second modulation frequency Fb, or low frequency. The device in accordance with the invention may advantageously but not necessarily by adapted to enable the operator to choose the modulation frequency. The latter would naturally choose the high and low frequencies in accordance with the method of the invention.

In FIG. 6 the excitation means are represented in a manner that is not limiting by an argon laser 30 with which is associated a modulator 31, The modulator may be of the kind producing sinusoidal modulation of the amplitude of the corresponding laser radiation, for example a modulator system using rotating polarizers. As it is not necessary for the modulation to be perfectly sinusoidal it is also possible to apply modulation by means of repetitive pulses provided that appropriate synchronous detection is also implemented. In this case the light source may consist of flash lamps, a "Q-switch" type pulse modulated laser or the like.

An optical system 32 focuses the modulated beam onto the sample 1.

The device further comprises means 33–35 for detecting the thermal signal generated by the sample 1 and means 36 for measuring the amplitudes Th, Tb and the phase shifts $\phi h$ and $\phi b$ of the thermal signal relative to the amplitude modulation excitation signal. To give a non-limiting example, the reference number 33 designates a silvered spherical mirror serving to focus the thermal signal onto an infra red detector cell 34 which delivers a detected signal to a synchronous detector system 35 controled directly by the modulator 31. The measuring means 36 may comprise, for example, analog-to-digital converter means and means for storing the digitized measured values.

Computing means are also provided for calculating the diffusivity A, the thickness d and the absorptivity B of the surface layer, according to the method already described, conforming to the method in accordance with the invention, as well as the thermal resistance R of the interface between the two layers.

The storage and computing means and possibly even the analog-to-digital conversion means may advantageously consist in a microcomputer denoted 36 in FIG. 6, as available on the commercial market and provided with its peripheral devices, denoted by reference numeral 37, such as backing store, printer, visual display unit. As can be seen in FIG. 6 the microcomputer 36 is connected to the modulator 31 to synchronize emission of the excitation beam, the synchronization being relayed from the modulator 31, for example, at the level of the synchronous detector system 35, which delivers the value masurement analogue signal directly to the microcomputer 36.

In an advantageous but non-limiting way the computing means may comprise tables for transcoding the aforementioned arrays of values to determine the values of the physical parameters, as previously described. The computing means may comprise programs for determining the values of the aforementioned parameters from the measured values and the arrays of values. The transcoding tables and/or the computation programs may be held in read only memory, 360 of course, in the known manner.

Likewise, the tables and/or the computational programs may advantageously comprise a "menu" type program enabling parameters relating to the material to be analyzed to be entered and chosen by operator action. Specifically, it would be beneficial to have the facility to enter the nature of the surface layer, in clear language or in code, and the value estimated by the operator for the surface layer thickness for a given type of product, the aforementioned program then being able either to display the values of the high frequency Fh and low frequency Fb to be used or to select these frequencies automatically.

FIG. 6 shows the focusing of a narrow aperture laser beam onto a specific point on the sample, the thermal radiation generated by this being in turn focused onto the sensitive cell of an infra red detector, It is to be understood that the device of the invention may equally well be adapted to excite all of the surface of the surface layer or at least of a part of this surface covering all of one of its dimensions, in particular, in the case of a strip form material, the infra red detector then being replaced by a scanning type infra red detector device such as a televison type scanning infra red cameras, this device making it possible to analyze point by point all of the surface of the excited or illuminated sample. In this case detection synchronized to the scanning of the camera makes possible point by point analysis and measurement of the corresponding values at these points.

The method and the device of the invention have been described for the most part in relation to a two-layer material However, the analysis of a single-layer material lies within the scope of the present invention to the extent that a single-layer slab of material may always be considered as the surface layer with the base layer consisting of the ambient air.

The method of the invention and the device for implementing it are particularly advantageous because of the flexibility with which they can be used; specifically they provide for measuring surface layer thicknesses varying between a few micrometers and a few hundred micrometers.

Also, and as previously mentioned in this description, the scope of application of the method and device of the invention is extremely varied since it relates not only to industry, mechanical engineering and manufacturing, but also to medical imaging and analysis.

There is claimed:

1. Method of analyzing and measuring by thermal radiometry physical parameters of a layered material comprising a base layer and a surface layer, wherein to determine said parameters such as the absorptivity B and diffusivity A of said surface layer and the thermal resistance R of the interface between said two layers of a sample relative to a reference sample having a surface layer of known thickness d' the method consists in:

(a) exciting the surface layer side of said reference sample by means of a flux of thermal energy amplitude modulated according to a periodic law at a high frequency Fh very much greater than a value for which the thermal diffusion length l' of said surface layer is small relative to the thickness d' of said surface layer.

(b) detecting the thermal signal generated by said reference sample as a result of absorption and measuring the amplitude Th and phase shift $\phi$h of said thermal signal relative to the amplitude modulation excitation signal;

(c) exiting the surface layer side of said reference sample by means of a flux of thermal energy amplitude modulated according to a periodic law at a low frequency Fb such that said thermal diffusion length l' of said surface layer is approximately equal to its thickness;

(d) detecting the thermal signal generated by said reference sample in response to said excitation and measuring the amplitude Tb of said thermal signal; and (e) determining the parameter A from the ratio of the amplitudes of said thermal signal at said low and said high frequencies, Tb/Th, and from the equation:

$$B\sqrt{A} = \frac{\tan\left(\phi + \frac{\pi}{2}\right)}{1 - \tan\left(\phi + \frac{\pi}{2}\right)} \sqrt{4\pi Fh}$$

by interpolation using an array of values $d\sqrt{A}$, Tb/Th, $B\sqrt{A}$ and where $\phi$ represents the measured phase shift and then determining the parameter B.

2. Method of analyzing and measuring by thermal radiometry physical parameters of a layered material comprising a base layer and a surface layer, parameters such as the thickness d, absorptivity B and diffusivity A of said surface layer and the thermal resistance R of the interface between said two layers, wherein to determine the thickness d of said surface layer when said thermal resistance R is low the method consists in:

(a) submitting a reference sample of the material having a surface layer of known thickness d' to the method according to claim 1, said reference sample serving to determine the diffusivity A and the absorptivity B of said surface layer;

(b) submitting a sample of material to the steps of:
(i) detecting the thermal signal generated by said sample of material as a result of absorption and measuring the amplitude Th and phase shift $\phi$h of said thermal signal relative to the amplitude modulation excitation signal:

(ii) exciting the surface layer side of said sample of material by means of a flux of thermal energy amplitude modulated according to a period law at a low frequency Fb such that said thermal diffusion length l' of said surface layer is approximately equal to its thickness:

(iii) detecting the thermal signal generated by said sample of material in response to said excitation and measuring the amplitude Tb of said thermal signal; and (c) determining the thickness d of said surface layer of said sample of material from said array of values $d\sqrt{A}$, Tb/Th, $B\sqrt{A}$.

3. Method according to claim 2, wherein said sample of material is subjected to a step of detecting the thermal signal generated by said reference sample in response to the excitation and measuring the amplitude Tb of the thermal signal and wherein said step further involves:

(a) measuring the phase shift $\phi$b of said thermal signal relative to the amplitude modulation excitation signal when $\phi$b represents the phase shift at the low frequency Fb of the amplitude modulation excitation signal; and (d) determining the thickness d of said surface layer of said sample of material from an array of value $\phi$,R,d where $\phi$ represents the value of said phase shift.

4. Method of analyzing and measuring by thermal radiometry physical parameters of a layered material comprising a base layer and a surface layer, parameters such as the thickness d, absorptivity B and diffusivity A of said surface layer and the thermal resistance R of the interface between said two layers, wherein to determine the absorptivity B of said surface layer the method consists in:

(a) submitting a reference sample of the material of known thickness d' to the method according to claim 1, said reference sample serving to determine at least the diffusivity A of said surface layer;

(b) exciting the surface layer side of said material by means of a flux of thermal energy amplitude modulated according to a period law at a frequency substantially equal to said frequency Fh;

(c) detecting the thermal signal generated by said material as a result of absorption and measuring the phase shift $\phi$h of said thermal signal relative to the amplitude modulation excitation signal; and (d) determining the absorptivity B of said surface layer from the equation:

$$B = \frac{\tan\left(\phi + \frac{\pi}{2}\right)}{1 - \tan\left(\phi + \frac{\pi}{2}\right)} \sqrt{\frac{4\pi Fh}{A}}$$

where $\phi$ is the measured phase shift.

5. Method of analyzing and measuring by thermal radiometry physical parameters of a layered material comprising a base layer and a surface layer, parameters such as the thickness d, absorptivity B and diffusivity A of said surface layer and the thermal resistance R of the interface between said two layers, wherein to determine the diffusivity A of said surface layer the method consists in:
  (a) submitting a reference sample of the material of known thickness d' to the method according to claim 1, said reference sample serving to determine at least the absorptivity B of said surface layer;
  (b) exciting the surface layer side of said material by means of a flux of thermal energy amplitude modulated according to a periodic law at a frequency substantially equal to said frequency Fh;
  (c) detecting the thermal signal generated by said material as a result of absorption and measuring the phase shift $\phi h$ of said thermal signal relative to the amplitude modulation excitation signal; and
  (d) determining the diffusivity A of said surface layer from the equation:

$$A = \frac{1}{B^2} \left( \frac{\tan\left(\phi + \frac{\pi}{2}\right)}{1 - \tan\left(\phi + \frac{\pi}{2}\right)} \right)^2 \cdot 4\pi Fh$$

where $\phi$ is the measured phase shift.

6. Method of analyzing and measuring by thermal radiometry physical parameters of a layered material comprising a base layer and a surface layer, wherein after the thickness d, absorptivity B and diffusivity A have been determined by the method according to any one of claims 1 through 4, to determine the thermal resistivity R of the interface between said two layers the method consists in:
  (a) exciting the surface layer side of said material by means of a flux of thermal energy amplitude modulated according to a periodic law at a frequency substantially equal to said frequency Fb;
  (b) detecting the thermal signal generated by said material as a result of absorption and measuring the phase shift $\phi b$ of said thermal signal relative to the amplitude modulation excitation signal; and
  (c) determining said thermal resistance R of said interface from an array of values $\phi$, R.

7. Method according to claim 1, 2, 4 or 5 wherein the steps during which said sample is excited by means of a flux of thermal energy amplitude modulated at said low and said high frequency are simultaneous.

8. Method according to claim 1, 2, 4 or 5, wherein said steps during which said sample is excited are successive in a predetermined sequence of excitation at frequencies Fb, Fh or at frequencies Fh, Fb.

9. Method according to claim 1, 2, 4 or 5 comprising a phase calibration stage consisting in subjecting to the excitation flux of thermal energy a calibrated sample that is thermally thick and absorbs only at its surface, said calibrated sample producing a phase shift of 45° between said thermal signal generated by said material as a result of absorption and said excitation signal.

10. Method according to claim 1, 2, 4 or 5 wherein said excitation flux of thermal energy is generated by means of electromagnetic radiation that can be absorbed by said surface layer.

11. Method according to claim 10, wherein said excitation flux of thermal energy is generated by means of electromagnetic radiation and the wavelength of said radiation corresponds to the semi-transparency band of said surface layer.

12. Method according to claim 1, 2, 4 or 5 wherein the steps during which said sample is excited by means of a flux of thermal energy amplitude modulated at said low and said high frequency are successive.

13. Method according to claim 1, 2, 4 or 5 wherein said excitation flux of thermal energy is generated by means of a flow of heat-exchange fluid.

14. Method according to claim 1, 2, 4 or 5 wherein said excitation flux of thermal energy is generated by means of heating by means of the Joule effect.

15. Device for analyzing and measuring by thermal radiometry physical parameters of a layered material comprising a base layer and a surface layer, comprising:
  (a) means for exciting the surface layer side of a sample of the material by means of a flux of thermal energy amplitude modulated according to a periodic law at least at a high frequency Fh and a low frequency Fb, said high frequency Fh being very much higher than a frequency for which the thermal diffusion length of said surface layer is small relative to the thickness of said surface layer and said low frequency Fb being such that the thermal diffusion length of said surface layer is approximately equal to its thickness;
  (b) means for detecting the thermal signal generated by said sample and means for measuring the amplitude Th, Tb and the phase shift $\phi h$, $\phi b$ of said thermal signal relative to the amplitude modulation excitation signal;
  (c) means for storing said signals and computing: the diffusivity A of said surface layer from the ratio of the amplitudes of said thermal signal at said low and said high frequencies, Tb/Th, and the equation:

$$B\sqrt{A} = \frac{\tan\left(\phi + \frac{\pi}{2}\right)}{1 - \tan\left(\phi + \frac{\pi}{2}\right)} 4\pi Fh$$

where $\phi$ represents the measured phase shift, by interpolation from an array of values $d/\sqrt{A}$, Tb/Th, $B\sqrt{A}$, and then computing the absorptivity parameter B; the thickness d of said surface layer;

the absorptivity B of said layer from the equation:

$$B = \frac{\tan\left(\phi + \frac{\pi}{2}\right)}{1 - \tan\left(\phi + \frac{\pi}{2}\right)} \sqrt{\frac{(4\pi Fh)}{A}}$$

the diffusivity A of said surface layer from the equation:

$$A = \frac{1}{B^2} \left( \frac{\tan\left(\phi + \frac{\pi}{2}\right)}{1 - \tan\left(\phi + \frac{\pi}{2}\right)} \right)^2 \cdot 4\pi Fh$$

the thermal resistance R of the interface between said two layers from said array of values $\phi$ and R.

16. Device according to claim 15, wherein said computing means comprises tables for transcoding said arrays of values to determine values for the diffusivity A, absorptivity B and thickness d of said surface layer and the thermal resistance R of the interface between said two layers.

17. Device according to claim 16 comprising read only memory storing said transcoding tables.

18. Device according to claim 16, wherein said transcoding tables comprise a menu program said program comprising control orders for selecting and introducing parameters relating to the material to be analyzed.

19. Device according to claim 15 wherein the thickness d of said surface layer is computed from said array of values $\phi$, R and d, where $\phi$ represents the measured phase shift.

20. Device according to claim 15 wherein the thickness d of said surface layer is computed from said array of values $d/\sqrt{A}$, $T_b/T_h$, $B\sqrt{A}$.

21. Device according to claim 12, wherein said computing means comprise programs for computing values for the diffusivity A, absorptivity B and thickness d of said surface layer and the thermal resistance R of said interface between said two layers from the measured values and said arrays of values.

22. Device according to claim 21, comprising read only memory storing said programs.

* * * * *

UNITED STATES PATENT AND TRADEMARK OFFICE
CERTIFICATE OF CORRECTION

PATENT NO. : 4,875,175
DATED : 10/17/89
INVENTOR(S) : Egee et. al.

It is certified that error in the above-identified patent and that said Letters Patent is hereby corrected as shown below:

| | |
|---|---|
| col. 02, line 26 | delete "period" insert --periodic-- |
| col. 04, line 65 | delete "period" insert --periodic-- |
| col. 05, line 14 | delete "maens" insert --means-- |
| col. 05, line 15 | delete "period" insert --periodic-- |
| col. 08, line 17 | delete "teh" insert --the-- |
| col. 08, line 27 | delete "(Fg, Fh)" insert --(Fb, Fh)-- |
| col. 09, line 31 | delete "period" insert --periodic-- |
| col. 10, line 42 | delete "," insert --.-- |
| col. 10, line 49 | delete "cameras" insert --camera-- |
| col. 12, lines 5, 46 | delete "period" insert --periodic-- |
| col. 12, line 27 | delete "(d)" insert --(b)-- |

Signed and Sealed this

Twenty-third Day of July, 1991

*Attest:*

HARRY F. MANBECK, JR.

*Attesting Officer*   *Commissioner of Patents and Trademarks*